(12) United States Patent
Ihara

(10) Patent No.: US 8,408,705 B2
(45) Date of Patent: Apr. 2, 2013

(54) SYSTEM FOR OBSERVING CORNEA FOR TRANSPLANTATION

(75) Inventor: Hiroaki Ihara, Hyogo (JP)

(73) Assignee: Konan Medical, Inc., Hyogo (JP)

( * ) Notice: Subject to any disclaimer, the term of this patent is extended or adjusted under 35 U.S.C. 154(b) by 0 days.

(21) Appl. No.: 12/925,617

(22) Filed: Oct. 26, 2010

(65) Prior Publication Data

US 2011/0102743 A1    May 5, 2011

(30) Foreign Application Priority Data

Oct. 29, 2009 (JP) ................. 2009-249530
Aug. 3, 2010 (JP) ................. 2010-174909

(51) Int. Cl.
*A61B 3/14* (2006.01)
*A61B 3/10* (2006.01)
(52) U.S. Cl. .................. 351/206; 351/210; 351/221
(58) Field of Classification Search .......... 351/205–206, 351/210, 221, 245–247
See application file for complete search history.

(56) References Cited

U.S. PATENT DOCUMENTS

| | | | |
|---|---|---|---|
| 5,523,213 A | 6/1996 | Takahashi et al. | |
| 5,956,123 A * | 9/1999 | Abe et al. | 351/216 |
| 6,201,984 B1 * | 3/2001 | Funda et al. | 600/407 |
| 2005/0213037 A1 * | 9/2005 | Abdullayev et al. | 351/221 |

FOREIGN PATENT DOCUMENTS

| | | |
|---|---|---|
| JP | 6-274600 | 9/1994 |
| JP | 8-243082 | 9/1996 |
| JP | 2000-033096 | 2/2000 |
| JP | 3922486 | 5/2007 |

* cited by examiner

*Primary Examiner* — Dawayne A Pinkney
(74) *Attorney, Agent, or Firm* — Jordan and Hamburg LLP

(57) ABSTRACT

The present invention is directed to a system for observing a cornea for transplantation which includes: an illumination means for illuminating the cornea for transplantation contained in a container; an entire-view imaging means for imaging the substantial entirety of the interior of the container; a position adjusting means for adjusting the position and angle of the cornea for transplantation; a magnified-view imaging means for imaging a magnified view of the cornea for transplantation illuminated by the illumination means; an image display means for displaying each image taken by the entire-view imaging means and the magnified-view imaging means; and an image control means for controlling each image.

5 Claims, 5 Drawing Sheets

SYSTEM FOR OBSERVING CORNEA FOR TRANSPLANTATION

TECHNICAL FIELD

The present invention relates to an observation system of a cornea for transplantation capable of efficiently conducting observation, photographing, measurement and the like of a cornea for transplantation.

BACKGROUND ART

In conventional ophthalmic medical care for corneal transplantation, special observation apparatuses such as microscopes capable of observing the thickness of a cornea for transplantation, the size, the conditions and the like of corneal cells, and photographing or measurement of the same have been prevailing for achieving safe and optimal transplantation of the cornea. As an observation apparatus of a cornea for transplantation, for example, a microscope has been known in which the cornea for transplantation contained in a container such as a sample vial or a dedicated vessel for a cornea for transplantation is mounted together with the container etc., on an optical axis of a microscope to carry out observation. As such a microscope, a specular microscope has been ordinarily used.

Observation or the like of such a general cornea for transplantation is carried out with a specular microscope by observing the cornea for transplantation contained in a container from the bottom face side of the container. Thus, since a specular microscope is used for observing a cornea for transplantation, it is difficult to specify the direction in which the cornea for transplantation should be moved for obtaining a magnified view when any magnified view is not captured. In addition, even in the case in which a magnified view is captured, it is difficult to ascertain which part of the cornea for transplantation is shown by this magnified view.

Such difficulties result from the state of the cornea for transplantation contained in the sample vial filled with a chemical liquid without being fixed, as it is not necessarily positioned at the center of the vessel. In addition, due to the construction of the specular microscope, it is necessary to move the cornea for transplantation as a subject to an intersection point of the axis of the irradiated light and the axis of the observed light in transversal and horizontal directions as well as vertical direction for adjustment. Particularly, in the case in which, for example, the vessel cannot be visually observed from above due to a lid of the sample vial or the like not being transparent, or the cornea is likely to move in the vessel, the magnified view captured frequently corresponds to the end of the cornea or out of the cornea. Accordingly, there exist disadvantages of necessity of spending energy for position adjustment in order for the observer to observe the cornea, thereby necessitating waste of labor and time for observation.

Under such circumstances, for the purpose of overcoming the aforementioned disadvantages, an observation apparatus provided with a positioning assistance means such as a mirror or camera that reflects the observed view region, on the back face side of the sample vial has been also proposed in order to ascertain the magnified target region in this observation apparatus (see Japanese Patent No. 3922486). However, it is necessary to ascertain the position by peering down the mirror, or to ascertain the position by changing a low-magnification lens into the optical system according to the positioning assistance means, and thus the workability is not necessarily superior due to, for example, needs for carrying out this operation each time following changing the observation positions. Therefore, even in commercially available apparatuses for observing a cornea for transplantation provided with a positioning assistance means, the positioning assistance means itself has not been fully utilized under current situations.

SUMMARY OF THE INVENTION

Problems to be Solved by the Invention

The present invention was made in view of the foregoing disadvantages, and an object of the invention is to provide a system for observing a cornea for transplantation that enables the position of the cornea for transplantation to be ascertained easily and concurrently with observation of the magnified view, and also enables positioning for obtaining a magnified view, and determination of the position of the resulting magnified view to be easily carried out.

Means for Solving the Problems

One aspect of the invention for solving the foregoing problems provides a system for observing a cornea for transplantation comprising:
an illumination means for illuminating the cornea for transplantation contained in a container,
an entire-view imaging means for imaging the substantial entirety of the interior of the container,
a position adjusting means for adjusting the position and angle of the cornea for transplantation,
a magnified-view imaging means for imaging a magnified view of the cornea for transplantation illuminated by the illumination means,
an image display means for displaying each image taken by the entire-view imaging means and the magnified-view imaging means, and
an image control means for controlling each image.

The system for observing a cornea for transplantation is provided with an illumination means for illuminating the cornea for transplantation contained in a container, an entire-view imaging means for imaging the substantial entirety of the interior of the container including the illuminated region, and an image display means for displaying the image. Therefore, according to the present system, with reference to the illuminated region, adjustment of the position and angle of the cornea for transplantation by the position adjusting means is enabled while observing the image taken by the entire-view imaging means. Therefore, positioning of the cornea for transplantation, i.e., a subject of observation can be executed with ease and without fail. Additionally, according to the present system, the observation of the image display means by the observer enables instantaneous and certain determination to be made as to which region of the subject is captured by the magnified-view imaging means, without need of additional operation and labor.

In addition, since the system for observing a cornea for transplantation has an image control means for controlling each image described above, display of the image on the image display means can be controlled by this image control means. Specifically, according to the system for observing a cornea for transplantation, for example, switching of the display size of the entire image and the magnified image on the image display means, adjustment of the brightness and the like for the purpose of facilitating observation of each image, display of multiple magnified images, and the like can be performed, and thus efficiency of observation and the like of the cornea for transplantation can be significantly improved.

It is preferred that the system for observing a cornea for transplantation has an image analysis means for analyzing the image taken by the magnified-view imaging means. Due to thus having an image analysis means of the magnified image, the system for observing a cornea for transplantation enables the workability to be significantly improved as, for example, the cell density etc., can be measured along with the observation.

It is preferred that the system for observing a cornea for transplantation further has a temperature measuring means of the container and/or the cornea for transplantation contained in the container. The cornea for transplantation may have been stored at a low temperature, and obtaining the magnified view by means of the specular microscope may be difficult when the temperature has been kept low. However, according to the system for observing a cornea for transplantation, the temperature of the cornea for transplantation upon observation can be easily measured, whereby defective observation resulting from the low temperature conditions can be prevented.

It is to be noted that the system for observing a cornea for transplantation preferably has a specular microscope which includes the illumination means and the magnified-view imaging means, wherein the specular microscope may have a light source, a condenser lens, a slit and an objective lens in this order as an illumination optical system, and may have an objective lens and an observed-portion imaging camera as an observation optical system. Note that the light source of this specular microscope may be used as an illumination means.

Since the system for observing a cornea for transplantation has a specular microscope which includes the illumination means and the magnified-view imaging means, and also has a position adjusting means and an entire-view imaging means, imaging of the magnified view of the cornea can be more efficiently carried out with a specular microscope accompanied by difficulties in adjustment in terms of (1) moving the cornea for transplantation, i.e., a subject of observation onto the intersection point of the light path of the illumination optical system and the light path of the observation optical system, and (2) adjusting the slope of the cornea for transplantation for obtaining a specular reflective light in a predetermined direction.

Effects of the Invention

As explained in the foregoing, the position of the cornea for transplantation can be ascertained easily and concurrently with observation of the magnified view, and also positioning for obtaining a magnified view, and determination of the position of the resulting magnified view can be easily carried out according to the system for observing a cornea for transplantation of the present invention. In addition, according to the system for observing a cornea for transplantation of the present invention, analysis of the resulting magnified image can be also carried out easily.

DETAILED DESCRIPTION OF THE INVENTION

[Mode for Carrying Out the Invention]

Hereinafter, the system for observing a cornea for transplantation of the present invention is explained in detail with appropriate reference to the drawings.

Figure 1:
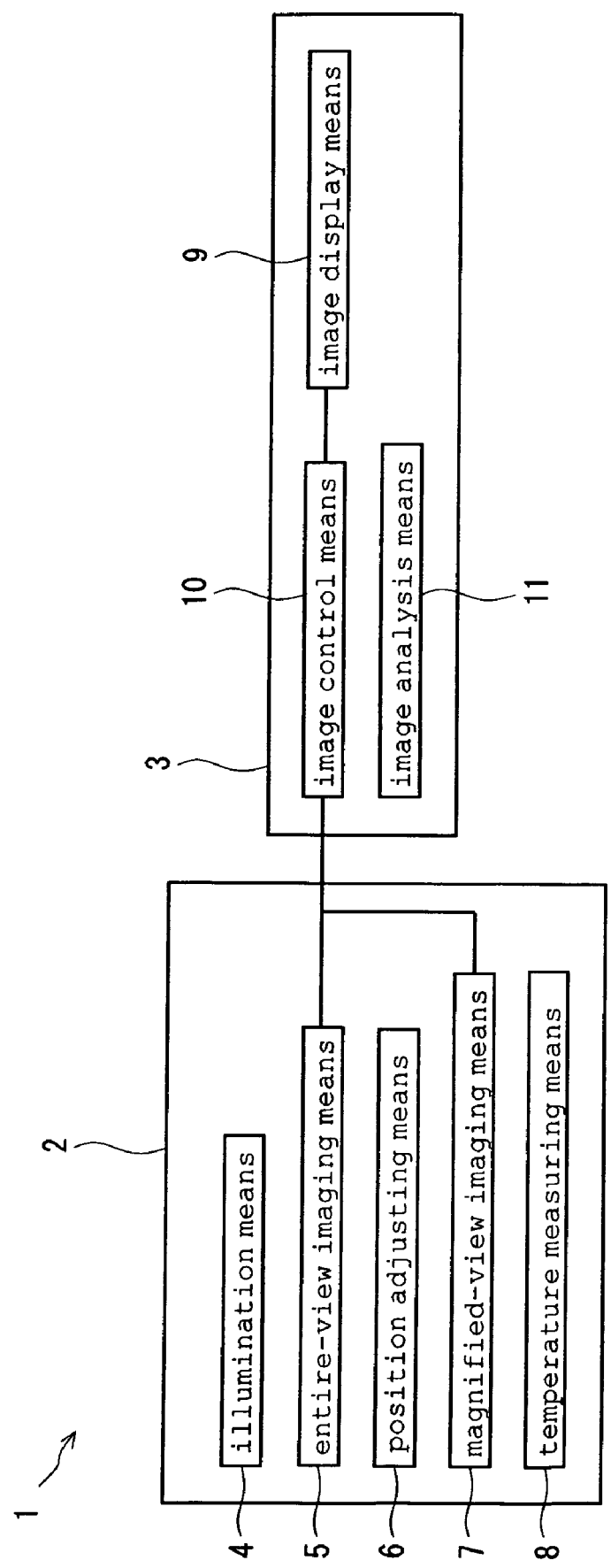
FIG. 1 shows a block diagram illustrating a construction of a system for observing a cornea for transplantation according to one embodiment of the present invention.

A system for observing a cornea for transplantation 1 shown in FIG. 1 has an observation apparatus 2, and a computer 3 connected to the observation apparatus 2.

The observation apparatus 2 has an illumination means 4, an entire-view imaging means 5, a position adjusting means 6, a magnified-view imaging means 7 and a temperature measuring means 8. Additionally, the illumination means 4, the entire-view imaging means 5, the position adjusting means 6, the magnified-view imaging means 7 and the temperature measuring means 8 in the observation apparatus 2 are constructed so as to be controllable automatically or manually. Moreover, the computer 3 is provided with an image display means 9, an image control means 10 and an image analysis means 11.

Figure 2:
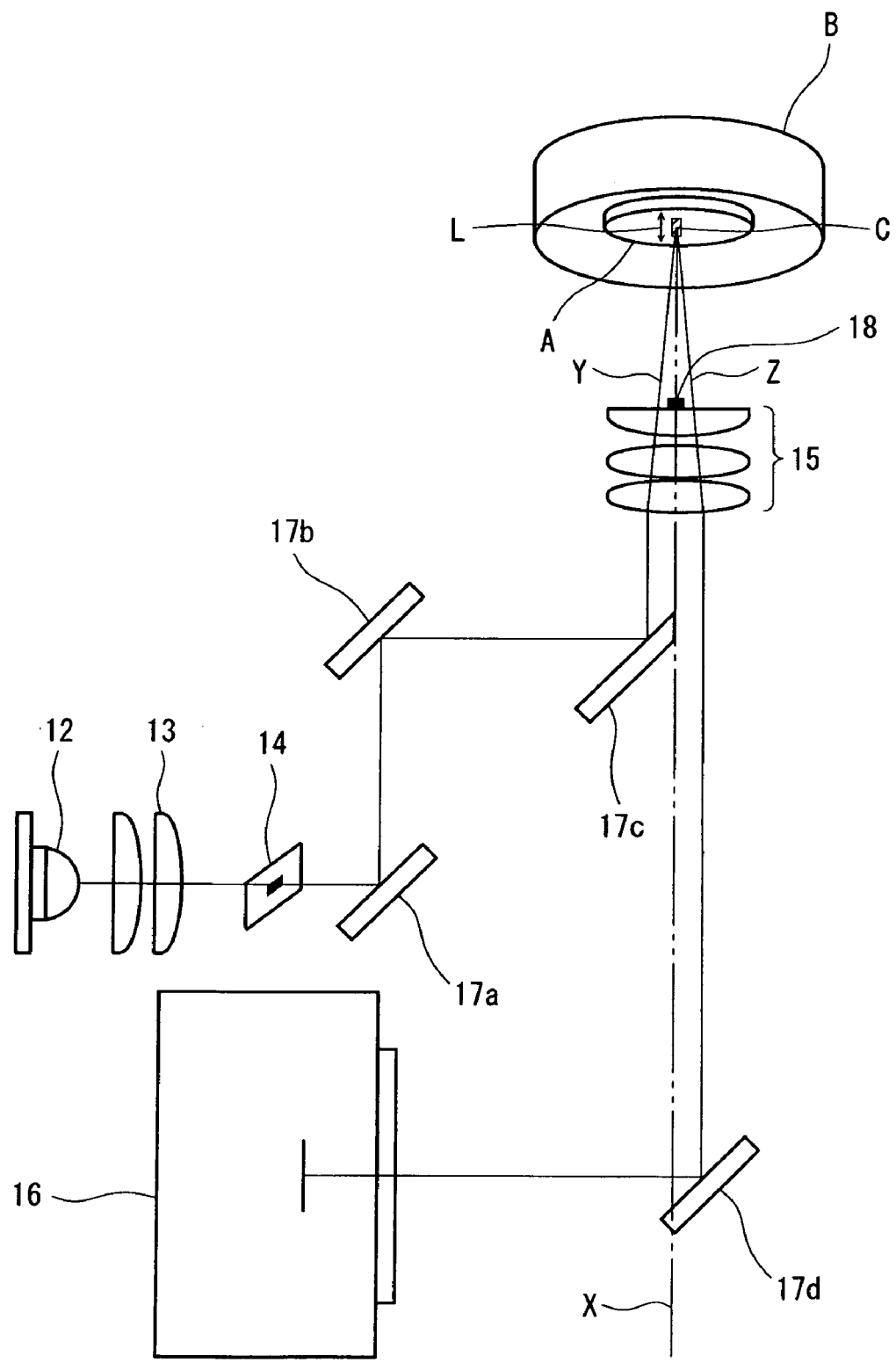
FIG. 2 shows a view illustrating an optical system of the system for observing a cornea for transplantation shown in FIG. 1.

The optical system according to the present system for observing a cornea for transplantation 1, i.e., the optical system according to the specular microscope that includes the illumination means 4 and the magnified-view imaging means 7 in the observation apparatus 2 is first explained with reference to FIG. 2.

The specular microscope has a light source 12, a condenser lens 13, a slit 14 and an objective lens 15 in this order as an illumination optical system, as well as an objective lens 15 and an observed-portion imaging camera 16 as an observation optical system, and further has a plurality of mirrors 17 provided ad libitum between the condenser lens 13 and the observed-portion imaging camera 16. It is to be noted that the specular microscope achieves size reduction of the optical system, and of the specular microscope in turn, by using lenses in common for the objective lens 15 of the illumination optical system, and the objective lens 15 of the observation optical system.

Additionally, the light source 12 is used as the illumination means 4 of the present system for observing a cornea for transplantation, whereas the observed-portion imaging camera 16 is used as the magnified-view imaging means 7.

The illumination optical system and the observation optical system of the specular microscope are explained in the following. Rays of light emitted from the light source 12 are converged by the condenser lens 13 and illuminate the slit 14 from behind. The rays of light are turned into a slit light, which has a cross sectional area of a line segment shape, by means of the slit 14.

As the light source 12, a halogen lamp, LED or the like may be used, and the LED that emits a monochromatic light is preferred. By using as the light source 12 LED that emits a monochromatic light, an image having a high contrast can be obtained due to the monochromatic light thus entered. Moreover, in LED that is used as the light source 12 and that emits a monochromatic light, the center wavelength of this monochromatic light may be 500 nm or higher and 550 nm or lower, and preferably 520 nm or higher and 530 nm or lower. According to the specular microscope, the image quality of the resulting magnified view can be further improved since the contrast is enhanced and the shading of the view of the corneal cells can be reflected when the center wavelength of the monochromatic light emitted from the LED light source falls within the above range.

The rays of light passed through the slit 14 illuminate on corneal endothelial cells in the cornea for transplantation A via the mirrors 17a, 17b and 17c, and through the objective lenses 15. When the rays of light pass through the objective lenses 15, the rays of light pass through a position away from the optical axis X of the objective lenses 15 to one side (in FIG. 2, left half side in the objective lenses 15), and exit from the objective lenses 15 as an outcoming light Y (the light path of this outcoming light Y being referred to as light path Y). This outcoming light Y enters angled to some extent with respect to the optical axis X (with a small angle of incidence) into the cornea for transplantation A, and then subjected to specular reflection in a symmetrical direction with respect to the optical axis X. The light thus subjected to specular reflection (reflected image of the cornea A) becomes an incoming light Z into the objective lenses 15 (the light path of this incoming light Z being referred to as light path Z), and passes through a position symmetrical to the outcoming light Y with respect to the optical axis X in the objective lenses 15 (in FIG. 2, right half side in the objective lenses 15). Accordingly, an image is formed via the mirror 17d on the observed-portion imaging camera 16. By designing a mirror 17c to be formed to have one sharp edge as shown in FIG. 2, and bringing the tip into line with the optical axis X, the illumination optical system can be separated from the observation optical system, whereby a still clearer magnified view can be obtained.

In the specular microscope, the slit 14 is provided such that a plane including the light path Y and the light path Z becomes perpendicular to the longitudinal direction of the cross section of the slit light that passes through the objective lenses 15. In other words, when the light path of the illumination optical system and the light path of the observation optical system are present on a single plane, for example, the slit 14 is provided in a perpendicular direction with respect to this plane. Note that the longitudinal direction L of the cross section of the slit light as an illuminated region C in FIG. 2 agrees with the longitudinal direction of the cross section of the slit light that passes through the objective lenses 15. According to this type of a specular microscope, by providing the slit 14 in such a direction, the specular reflective light on the front face and the specular reflective light on the back face from the cornea for transplantation A can be separated, and thus magnified views of the front face side and the back face side of the cornea for transplantation A can be clearly obtained, respectively.

Furthermore, a masking plate 18 is provided on the surface of the object side of the objective lens 15 in the optical system of the specular microscope. This masking plate 18 is capable of separating the outcoming light Y from the objective lens 15 and the incoming light Z into the objective lens 15, thereby enabling the resulting magnified view to be a still clearer image.

The observed-portion imaging camera 16 has a function of transferring and processing the image information, and is for example, a CCD camera (a camera having an integrated circuit for transferring and processing the image information using a charge coupled device). The magnified view data obtained by the observed-portion imaging camera 16 is output to the image control means described later, and displayed by the image display means.

Figure 3:
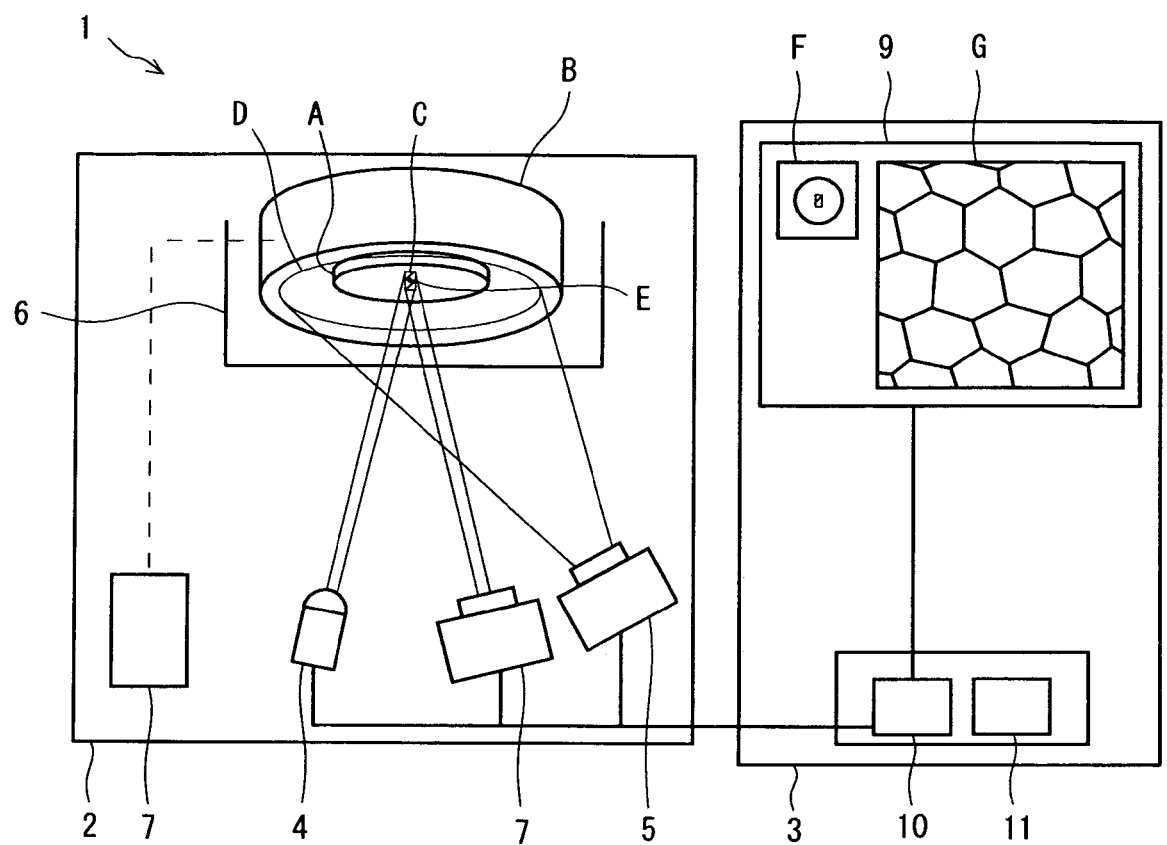
FIG. 3 shows a schematic view illustrating the construction of the system for observing a cornea for transplantation shown in FIG. 1.

Next, each construction of the present system for observing a cornea for transplantation 1 is explained in the order according to the schematic view shown in FIG. 3.

The illumination means 4 illuminates a part (hereinafter, may be also referred to as "illuminated region C") close to the center in the container B that contains the cornea for transplantation A, from the bottom face side of the container B. In other words, when the cornea for transplantation A is positioned near the center of the container B, the illumination means 4 illuminates this cornea for transplantation A. It should be noted that the bottom face portion of this container B is formed from a transparent material entity. As the illumination means 4, a halogen lamp, LED or the like used as the light source of the specular microscope as described above can be used.

With respect to the size and shape of the illuminated region C illuminated by the illumination means 4, a rectangle shape having a width of 0.3 mm or greater and 0.8 mm or less and a length of 2 mm or greater and 3 mm or less is preferred, and the illuminated region C may have, for example, a rectangle shape having a width of about 0.5 mm and a length of 2.5 mm. By irradiating a slit light in such a shape and size, the front-face reflected light and the back-face reflected light of the cornea for transplantation A having a thickness of about 0.5 mm can be suitably separated in the specular microscope.

The entire-view imaging means 5 takes an image of the substantial entirety in the container B including the scattering reflected light of the illuminated region C illuminated by the illumination means 4 (hereinafter, may be also referred to as "entire region D"), and outputs the image signal. Thus output image signal is entered into the computer 3. Since the entire region D imaged by the entire-view imaging means 5 includes the illuminated region C, the observer can recognize with ease and without fail through the image display means 9 as to whether or not the illuminated region C captures the cornea for transplantation A, and which part is captured. Therefore, the observer can execute positioning of the cornea for transplantation with ease and without fail by adjusting the position and angle of the cornea for transplantation A (container B) with the position adjusting means 6 described later while observing the image display means 9, and also can determine the position of the resulting magnified view on the cornea for transplantation. Although this entire-view imaging means 5 is not particularly limited, a well-known camera such as a finder camera can be used.

The position adjusting means 6 can adjust the position of the cornea for transplantation A contained in the container B in any of transversal, horizontal and vertical directions, and can also adjust the angle of the cornea for transplantation A contained in the container B. This position adjusting means 6 may be either manually or automatically operated.

As the magnified-view imaging means 7, the observed-portion imaging camera or the like in the specular microscope may be used. The magnified-view imaging means 7 takes an image of a magnified view of a portion (hereinafter, may be also referred to as "magnified target region E") of the illuminated region C illuminated with the aforementioned illumination means 4 from the bottom face side of the container B. More specifically, when the outcoming light Y from the objective lens 15 in FIG. 2 enters into the objective lens 15 as the incoming light Z by means of specular reflection due to the cornea for transplantation A, the magnified-view imaging means 7 can image the magnified view of the cornea for transplantation A illuminated with the illumination means 4. Additionally, the magnified-view imaging means 7 outputs the image signal. This output image signal is entered into the computer 3.

The temperature measuring means 8 measures the temperature of the container B and/or the cornea for transplantation A contained in the container B. Corneas for transplantation may have been stored at a low temperature, and obtaining the magnified view by means of the specular microscope may be difficult when the temperature has been kept low. However, according to the system for observing a cornea for transplantation, the temperature of the cornea for transplantation upon observation can be easily measured, whereby defective observation resulting from the low temperature conditions can be prevented. As the temperature measuring means 8, any well-known means such as an infrared ray thermometer, a radiation type thermometer, or other temperature sensor may be used.

This computer 3 specifically has a control unit composed of CPU, as well as ROM, RAM, a hard disc, a monitor, a key board, and the like. This computer 3 is constructed so as to function as the image control means 10 by controlling each unit based on the computer programs stored in the ROM, hard disc etc., and also as the image analysis means 11 by analyzing the image based on the computer program. In addition, the monitor of the computer functions as the image display means 9. Thus, according to the system for observing a cornea for transplantation 1, a general purpose computer can be used as the aforementioned image display means 9, image control means 10 and image analysis means 11 by separating the image display means 9, image control means 10 and image analysis means 11 from the observation apparatus 2.

The image display means 9 receives the input image signal, and displays at least an image (hereinafter, may be also referred to as "entire image F") taken as a scattering reflected light of the illumination means 4 (light source 12) with the entire-view imaging means 5, and an image (hereinafter, may be also referred to as "magnified image G") taken as a specular reflective light of the illumination means 4 (light source 12) with the magnified-view imaging means 7. The image display means 9 enables the observer to concurrently observe the entire image F and the magnified image G. Specifically, the observer can carry out observation, photographing or measurement and the like of the cell image of the cornea for transplantation A by observing the magnified image G. In addition, the observer can execute positioning for obtaining the magnified view with ease and without fail using the position adjusting means 6 while observing the entire image F, and can allow the magnified image G of the cornea for transplantation A to be displayed on the image display means 8. Moreover, the observer can carry out observation and the like of the magnified image G while determining as to which part of the cornea for transplantation A corresponds to the magnified image G, by observing the appearances of the cornea for transplantation A as the entire image F and the container B, and the position of the scattering reflected light from the slit illumination light reflected on the cornea for transplantation A and the container B. More specifically, according to the system for observing a cornea for transplantation 1, unnecessary operation such as peering down the subject part and the like as in the case of conventional observation apparatuses is obviated, and the image display means 9 enables instantaneous and certain determination as to whether the magnified-view imaging means 7 captures the subject utilizing the position of the scattering reflected light of the illuminated region C as a guide, and as to which region of the cornea for transplantation A corresponds to the obtained magnified view.

The image control means 10 receives the input image signal, and controls each image described above (entire image F and magnified image G). The control executed by this image control means 10 refers to adjustment of size, brightness, contrast and the like of each image, as well as other image processing. According to the system for observing a cornea for transplantation, for example, switching of the display size of the entire image F and magnified image G on the image display means 9, adjustment of the brightness for the purpose of facilitating observation of each image, display of multiple magnified images G, and the like can be performed using this image control means 10, whereby efficiency of observation of the cornea for transplantation A can be significantly improved.

The image analysis means 11 analyzes an image (magnified image G) taken by the magnified-view imaging means 7. Due to thus having the image analysis means 11 of the magnified image G, the system for observing a cornea for transplantation 1 has significantly improved workability as, for example, the cell density can be measured along with the observation. As such an image analysis means 11 for measuring the cell density, well-known semiautomatic or automatic analysis means disclosed in Japanese Unexamined Patent Application, Publication Nos. H06-274600, H08-243082 and the like may be employed. In connection with the semiautomatic analysis means, a center method may be adopted that enables all required data of the shape to be obtained by reproduction of the contour of each cell by entering into the computer only the center position of each cell from the corneal endothelial cell image.

Hereinafter, an example of an observation and analysis method of the cornea for transplantation A using the image display means 9, image control means 10 and image analysis means 11 is explained with reference to FIGS. 4A to 4D.

Figure 4A:
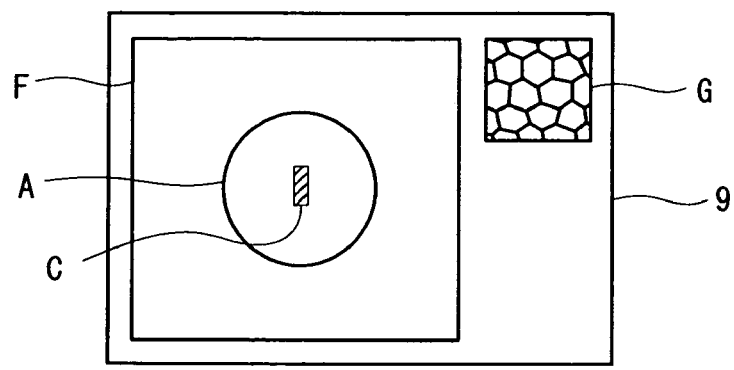
FIGS. 4A to 4d show schematic views respectively illustrating a display image on the image display means constructing the system for observing a cornea for transplantation shown in FIG. 1.
Figure 4B:
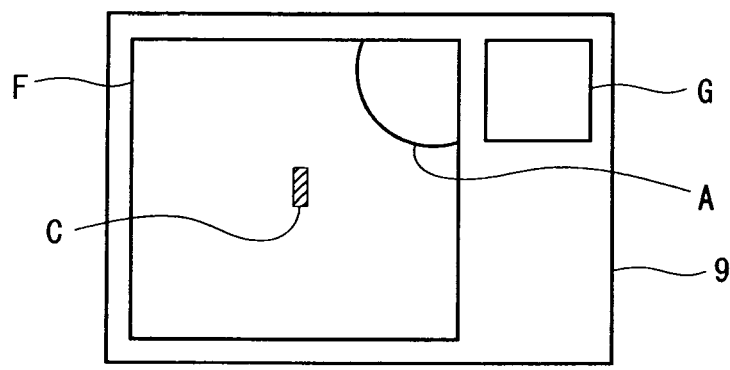

As shown in FIG. 4A, when the cornea for transplantation A is observed, the observer first controls the two images so as to allow the entire image F to be displayed as a magnified image on the image display means 9, and also allows the magnified image G to be displayed on a small screen with the image control means 10. Thus, by displaying the entire image F as a magnified image, the position of the cornea for transplantation A can be adjusted with the position adjusting means 6 while watching the entire image F, so as to situate the observation position of the cornea for transplantation A, as the observation target, on the illuminated region C. For example, when the cornea for transplantation A is not positioned on the illuminated region C as shown in FIG. 4B, the magnified-view imaging means 7 fails to capture the cornea for transplantation A as the magnified target region; therefore, the cornea for transplantation A is to be moved with the position adjusting means 6.

Additionally, even in the case in which the cornea for transplantation A is positioned on the illuminated region C, when the specular reflective light of the illumination means 4 does not agree with the light path of the observation optical system (light path Z in FIG. 2), the magnified view is not displayed in the magnified image G, whereby the observation fails. However, since positioning of the cornea for transplantation A on the illuminated region C can be ascertained by confirming the entire image F, the focal point can be regulated by adjusting the position and angle of the cornea for transplantation A by the position adjusting means 6.

In other words, according to the system for observing a cornea for transplantation 1, due to having the entire-view imaging means 5 and the image display means 9, which function as a finder for positioning of the cornea for transplantation A, a magnified view of the cornea for transplantation A can be efficiently obtained.

Relationships of the specular microscope as the magnified-view imaging means 7, the entire-view imaging means 5, and the position adjusting means 6 in the system for observing a cornea for transplantation 1 are now explained in detail with reference to FIG. 2, and the like. At an intersection point of the light path Y (light path corresponding to outcoming light from objective lens 15) and the light path Z (light path corresponding to incoming light to objective lens 15) in FIG. 2, when the surface of the cornea for transplantation A is positioned perpendicularly to the optical axis X, the specular reflective light by the surface of the cornea A of the outcoming light Y from the objective lens passes a light path that agrees with the light path Z. In this instance, the specular reflective light enters into the objective lens 15, and forms an image on the element of the observed-portion imaging camera 16. The endothelial cell image of a transparent cornea A is difficult to find unless an observation method according to this specular reflection method is employed.

Positioning is difficult according to such a specular reflection method in which a slit light is irradiated from an angle. More specifically, it is necessary to adjust both a position in a three dimensional direction toward the intersection point of the light path Y and the light path Z on the cornea for transplantation A, and a slope of the surface of the cornea for transplantation A. However, the system for observing a cornea for transplantation 1 has an entire-view imaging means 5, and this entire-view imaging means 5 enables a scattering reflected light to be observed at a low magnification. In other words, according to the system for observing a cornea for transplantation 1, when the subject (cornea for transplantation A) is present on an extension of the light path Y, the scattering reflected light can be confirmed with the entire-view imaging means 5 (entire image F), irrespective of the angle (slope) of the surface. More specifically, according to the system for observing a cornea for transplantation 1, in the state in which the position of the cornea for transplantation A was thus ascertained using the entire-view imaging means 5 (entire image F), a magnified view can be obtained by adjusting the position of the cornea for transplantation A in vertical, horizontal and transversal directions using the position adjusting means 6, and also adjusting the angle for the purpose of adjusting the orientation of the specular reflective light.

That is, general specular microscopes have difficulties in adjustment in terms of (1) moving the cornea for transplantation as a subject on the intersection point of the illumination optical system (light path Y) and the observation optical system (light path Z), and (2) adjusting the slope of the cornea for transplantation A for obtaining a specular reflective light in a predetermined direction (light path Z direction). Furthermore, according to general specular microscopes, (3) the difference of directions of the light path Y and the light path Z from the moving direction (vertical, horizontal and transversal directions) of the cornea for transplantation A (container B) by the position adjusting means 6 leads to more difficulty in the adjustment. However, according to the system for observing a cornea for transplantation 1, when the cornea for transplantation A is present on the illuminated region C as described above, scattering reflected light of the illumination means (light source) can be observed by the entire-view imaging means 5 (entire image F) irrespective of the angle of the cornea for transplantation A. Therefore, according to the system for observing a cornea for transplantation 1, in the state in which the position of the cornea for transplantation A is ascertained based on the entire image F by the entire-view imaging means 5, the magnified view can be obtained by adjusting the position of the cornea for transplantation A in vertical, horizontal and transversal directions using the position adjusting means 6, and also adjusting the angle for the purpose of adjusting the orientation of the specular reflective light, while confirming the magnified image G.

Figure 4C:
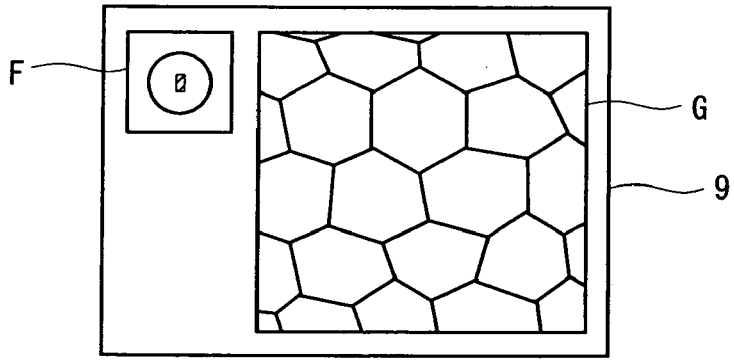

After the observer carries out adjustment so as to allow the cornea for transplantation A to be positioned on the illuminated region C with the position adjusting means 6 and fixes the region of the magnified view, control with the image control means 10 is executed such that the display size of the entire image F and the magnified image G is inverted as shown in FIG. 4C. By thus displaying the magnified image G on the image display means 9 to be magnified, details of the cell image of the cornea for transplantation A can be easily observed. In this step, determination as to which part of the cornea for transplantation A corresponds to the magnified image G as observed is enabled by displaying also the entire image F on a small screen. Additionally, also when magnification of the magnified image G is adjusted, magnification adjustment and position adjustment accompanied thereby can be carried out with ease and without fail by keeping the entire image F to be displayed.

Moreover, according to the system for observing a cornea for transplantation 1, for example, the brightness of the entire image F and the magnified image G can be changed, additionally. The entire image F does not necessitate a high brightness since it is satisfactory to reveal only a positional relationship between the cornea for transplantation A and the illuminated region C, and to the contrary, when the intensity is excessive, a negative effect such as difficulty in observation of the cornea for transplantation A may be exhibited due to the light intensity in excess. On the other hand, as for the magnified image G, it is necessary to clearly imaging the magnified view, and thus a high brightness is required. Therefore, according to the system for observing a cornea for transplantation 1, executing control such as decrease of the brightness of the entire image F and increase of the brightness of the magnified image G is enabled with the image control means 10, without adjusting the luminosity of the illumination means 4 and thus a suitable image can be concurrently provided on each screen.

Figure 4D:
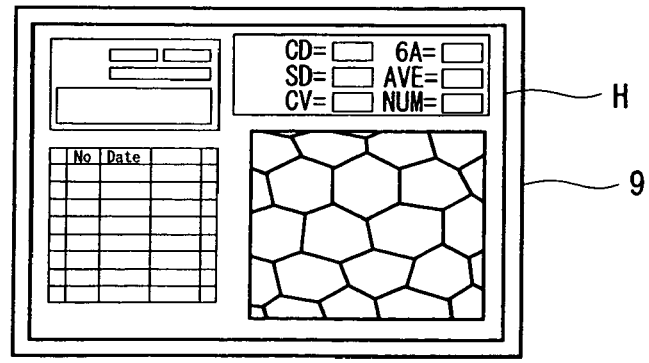

Furthermore, according to the system for observing a cornea for transplantation 1, the image on the analysis screen H of the image analysis means 11 can be also displayed on the image display means 9 using the image control means 10 as shown in FIG. 4D. This image analysis means 11 enables in the case of a semiautomatic analysis means, for example, measurement of the cell density and the like to be carried out while using the image display means 9. Additionally, since the entire image F can be displayed according to the system 1, analysis data of each part of the cornea for transplantation A can be obtained, and the system 1 also serves in performing advanced investigation and analysis of the cell level of the cornea.

As described in the foregoing, the observed cornea for transplantation A and the position of the magnified target region E can be displayed as the entire image F on the image display means 9 concurrently with the magnified image G, according to the system for observing a cornea for transplantation 1. Therefore, the positions of the observed cornea for transplantation A and the magnified target region E can be ascertained instantaneously and concurrently with the observation of the magnified image G according to the system 1; therefore, positioning for obtaining the magnified view, and determination of the position of the resulting magnified view can be easily carried out. Moreover, according to the system for observing a cornea for transplantation 1, adjustment of the size and brightness of each image, as well as analysis of the resulting magnified image G can be also carried out easily. Still more, due to having the image analysis means 11, various types of data and the like required for the cornea for transplantation A can be obtained by carrying out the observation and analyses in parallel according to the system for observing a cornea for transplantation 1 of the present invention, and thus operation efficiency is significantly improved.

Next, a specific structure of the observation apparatus 2 is explained with reference to FIG. 5. The observation apparatus 2 principally has the entire-view imaging means 5, the position adjusting means 6, a magnified-view imaging means and an illumination means (specular microscope 23), and a temperature measuring means 8.

The position adjusting means 6 has a holder 21 that receives the container B for containing the cornea for transplantation A, a supporting table 22 for supporting the holder 21, an encoder 24, a control means 25, a liquid crystal displaying unit 26, and a moving distance reset button 27.

The container B is a vessel for containing the cornea for transplantation A such as a sample vial, a dedicated vessel for cornea for transplantation, etc. The container B being filled with a chemical liquid contains the cornea for transplantation A, and is sealed tight such that a gas phase is not present at all. When the sample vial is directly used as the container B, the sample vial is preferably used after contained in a transparent vessel as disclosed in Japanese Patent No. 3922486.

The holder 21 receives the container B. The holder 21 either has a transparent material entity or cut away at the bottom face so as not to interfere the light path of the specular microscope 23 disposed on the beneath side. In addition, the lateral face of the holder 21 is formed to have a spherical shape so as to be held freely rotatably on the supporting table 22. Furthermore, the holder 21 has a collar segment 21a as a rotational movement control means, which extends from the upper edge portion toward the external side.

The supporting table 22 supports the holder 21 freely rotatably. The face of the supporting table 22 to be in contact with the holder 21 is formed to have a recessed curve shape such that the holder 21 becomes freely rotatable. However, each shape of the faces of the holder 21 and the supporting table 22 being in contact with each other is not limited to the shape described above as long as the holder 21 is supported to be freely rotatable. Additionally, the supporting table 22 has an adjusting mechanism constructed to be movable in vertical, horizontal and transversal directions although not shown in the figure. This adjusting mechanism is not particularly limited as long as it enables the movement as described above, and for example, a mechanism disclosed in Japanese Unexamined Patent Application, Publication No. 2000-33096, and the like may be used.

Since the observation apparatus 2 has the holder 21 and the supporting table 22 having such shapes and mechanisms (a structure in which the supporting table 22 receives the holder 21 freely rotatably, and an adjusting mechanism constructed so as to be movable in vertical, horizontal and transversal directions), it consequently has a position adjusting means for adjusting the position and the angle of the cornea for transplantation (holder 21) in vertical, horizontal and transversal directions.

Setting of the observation position of the cornea is facilitated according to the observation apparatus 2 by thus having each adjusting mechanism (adjusting mechanism for adjusting in vertical direction, horizontal direction and transversal direction) described above. One example of this each adjusting mechanism includes a mechanism to permit a sliding movement of a slidable face with a screw or the like.

In the observation apparatus 2, the slope of the observed face of the cornea can be changed such that the specular reflective light of the cornea for transplantation A in the container B can be obtained by rotatory movement of the holder 21 on the supporting table 22. However, when the rotational movement angle is great, the bottom of the container B and the cornea A incline so that error of magnification for observation may occur since distortion of refractive index is caused due to the inclination. Thus, according to the observation apparatus 2, due to having the rotational movement control means that restricts the rotational movement (angle of inclination) of the container B (holder 21), the angle of inclination of the cornea A and the container B can be restricted to fall within the allowable range, and the accuracy can be improved.

The supporting table 22 has as this rotational movement control means a stopper piece 22a provided to protrude upwardly on the upper edge of the part to be in contact with the holder 21. Since the supporting table 22 has the stopper piece 22a, the stopper piece 22a will be brought into contact with the collar segment 21a of the holder 21 when the holder 21 inclines above a certain level, and thus further inclination of the holder 21 is prevented whereby the angle of inclination holder 21 can be controlled.

This stopper piece 22a may be also mounted detachably. By replacing with other stopper piece 22a having a different height on the supporting table 22, the inclination can be adjusted to a permissible angle. In addition, the stopper piece as a rotational movement control means may be provided not on the supporting table 22 but on the holder 21. Alternatively, for example, several kinds of the collar segments 21a having different thicknesses of the holder 21 may be provided to be replaceable.

The specular microscope having the magnified-view imaging means 7 enables the cornea for transplantation A contained in the container B to be magnified and observed by means of the specular reflection image of the rays of light from a light source. In this specular microscope, the rays of the light source are irradiated on the cornea for transplantation A as a subject. In other words, the light source of the specular microscope per se serves as an illumination means 4 for illuminating the magnified target region.

In addition, according to this observation apparatus 2, when the cornea for transplantation A is observed, the supporting table 22 will be moved with the adjusting mechanism until the specular reflected image of the cornea for transplantation A is formed on the observed-portion imaging camera as described above provided inside. Therefore, according to this observation apparatus 2, the corneal thickness can be determined from the difference between the image formation positions of the corneal endothelial cell surface and the corneal epithelial cell surface (moving distance of supporting table 22 in vertical direction).

The encoder 24 detects the moving distance of the adjusting mechanism in at least vertical direction, and carries out data processing. In addition, the encoder 24 outputs the data of the moving distance to the control means. According to this observation apparatus 2, corneal thickness can be determined by the data processing of the moving distance of the adjusting mechanism in vertical direction with the encoder 24.

The control means 25 receives information data of each Moving distance from the encoder 24, and the moving distance and the corneal thickness based on the moving distance are calculated. It is to be noted that when the corneal thickness is calculated from the moving distance, correction may be carried out by calculating an error resulting from the refractive index differences also by the control means 25.

In addition, the control means 25 outputs the data of thus calculated corneal thickness, and the liquid crystal displaying unit 26 displays the data. Furthermore, the control means 25 receives the information entered from the moving distance reset button 27, and can reset the information of the moving distance. Additionally, the control means 25 receives the information entered from the light intensity adjusting volume 28, and then adjusts the output-voltage of the light source (not shown in FIG. 5) provided within the specular microscope 23.

The entire-view imaging means 5 is provided on the bottom side of the holder 21 similarly to the specular microscope 23. The entire-view imaging means 5 takes images of the illuminated region illuminated by the illumination means, and of the entire region, as described above.

The temperature measuring means 8 measures the temperature of the container B and/or the cornea for transplantation A contained in the container B. The temperature measured by the temperature measuring means 8 may be transferred to the control means 25, and also displayed on the liquid crystal displaying unit 26.

Figure 5:
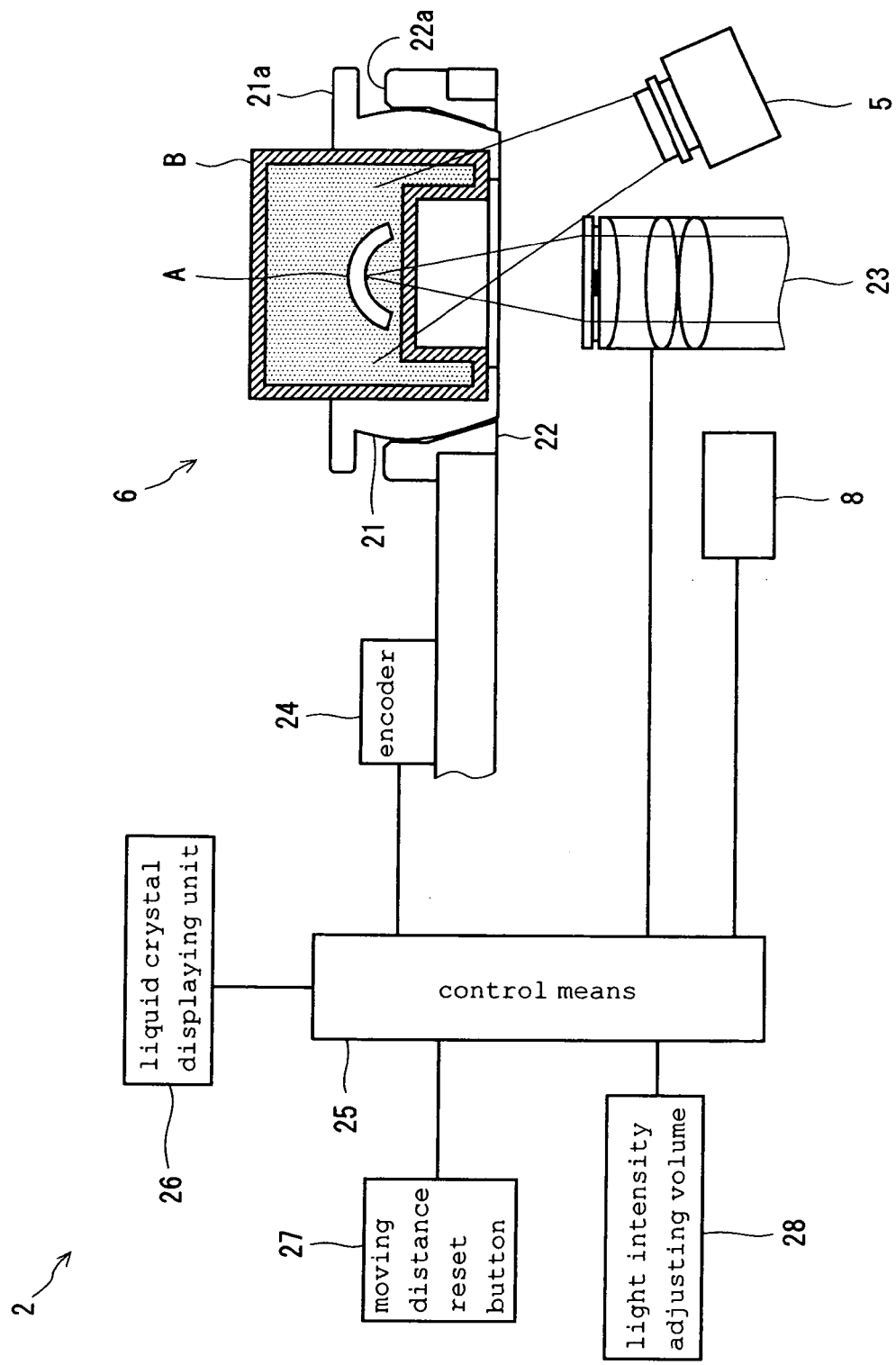
FIG. 5 shows a schematic view illustrating an observation apparatus constructing the system for observing a cornea for transplantation shown in FIG. 1.

Moreover, the illumination means not shown in FIG. 5 illuminates a region including the magnified target region. In the observation apparatus 2, the light source integrated into the specular microscope 23 serves as an illumination means as described above.

In this manner, the thickness of a cornea for transplantation A can be measured by reading out the difference between image formation positions of the corneal endothelial cell surface and the corneal epithelial cell face by means of a specular microscope using an adjusting mechanism in vertical direction, and the measured values can be easily confirmed by means of a liquid crystal display, according to the observation apparatus 2. Moreover, since the observation apparatus 2 has a rotational movement control means, the angle of inclination of a container B can be controlled, whereby occurrence of error of magnification for observation that results from the distortion of refractive index due to inclination is suppressed, and thus the accuracy of the measurement can be improved.

It should be noted that the system for observing a cornea for transplantation of the present invention is not limited to the foregoing embodiment. For example, at least one of an image control means, an image analysis means and an image display means may be integrated into the observation apparatus for use therein. Also, in the magnified-view imaging means, a microscope or the like other than the specular microscope may be used. In this case, a discrete illumination means may be also provided depending on the type and the like of the magnified-view imaging means.

INDUSTRIAL APPLICABILITY

As in the foregoing, the system for observing a cornea for transplantation of the present invention is utilized as a system for observation, photographing, measurement and the like of a cornea used for corneal transplantation following magnification.

DESCRIPTION OF THE NUMERALS AND SYMBOLS

1 system for observing a cornea for transplantation
2 observation apparatus
3 computer
4 illumination means
5 entire-view imaging means
6 position adjusting means
7 magnified-view imaging means
8 temperature measuring means
9 image display means
10 image control means
11 image analysis means
12 light source
13 condenser lens
14 slit
15 objective lens
16 observed-part imaging camera
17 mirror
18 masking plate
21 holder
21a collar segment
22 supporting table
22a stopper piece
23 specular microscope
24 encoder
25 control means
26 liquid crystal displaying unit
27 moving distance reset button
28 light intensity adjusting volume
A cornea for transplantation
B container
C illuminated region
D entire region
E magnified target region
F entire image
G magnified image
H analyzed image
L longitudinal direction
X optical axis
Y outcoming light from objective lens (light path)
Z incoming light to objective lens (light path)
P intersection point of light path Y and light path Z

The invention claimed is:

1. A system for observing a cornea for transplantation comprising:
    an illumination means fur illuminating the cornea for transplantation contained in a container, wherein reflected light of an illuminated region is scattered by the illumination means,
    an entire-view imaging means for imaging the substantial entirety of the interior of the container,
    a position adjusting means for adjusting the position and angle of the cornea for transplantation,
    a magnified-view imaging means for imaging a magnified view of the cornea for transplantation illuminated by the illumination means using a specular reflection method,
    an image display means for concurrently displaying each image taken by the entire-view imaging means and the magnified-view imaging means as live images, and
    an image control means for controlling each image.

2. The system for observing a cornea for transplantation according to claim 1 comprising an image analysis means for analyzing the image taken by the magnified-view imaging means.

3. The system for observing a cornea for transplantation according to claim 1 further comprising a temperature measuring means for measuring a temperature of at least one of the container and the cornea for transplantation contained in the container.

4. The system for observing a cornea for transplantation according to claim 1, wherein the entire-view imaging means comprises a first camera that captures a first field of view in an ongoing manner, and the magnified-view imaging means comprises a second camera distinct from the first camera and that captures a magnified field of view in an ongoing manner, and wherein the image display means concurrently display first imaging captured by the first camera and second imaging captured by the second camera, and wherein the position adjusting means is enabled to adjust the position and angle of the cornea causing a change in the second imaging while the first imaging and second imaging are concurrently displayed, so that the magnified field of view of the cornea may be obtained.

5. The system for observing a cornea for transplantation according to claim 1, wherein the entire-view imaging means images the substantial entirety of the interior of the container to obtain first imaging, while the magnified-view imaging means concurrently images the magnified view of the cornea to obtain second imaging, wherein the second imaging may be varied by the position adjusting means in response to the image control means so that the magnified-view imaging means obtains a magnified view of the cornea.

\* \* \* \* \*